United States Patent [19]

Bellut

[11] Patent Number: 4,898,984
[45] Date of Patent: Feb. 6, 1990

[54] PROCESS FOR PREPARING 3,5,5,-TRIMETHYL-4-HYDROXY-2-CYCLOHEXEN-1-ONE

[75] Inventor: Hans Bellut, Duelmen, Fed. Rep. of Germany

[73] Assignee: Huels Aktiengesellschaft, Marl, Fed. Rep. of Germany

[21] Appl. No.: 278,232

[22] Filed: Nov. 30, 1988

[30] Foreign Application Priority Data

Mar. 3, 1988 [DE] Fed. Rep. of Germany ....... 3806835

[51] Int. Cl.$^4$ ............................................. C07C 45/28
[52] U.S. Cl. ................................................... 568/342
[58] Field of Search ................ 568/342, 343, 344, 385

[56] References Cited

U.S. PATENT DOCUMENTS

| 3,931,327 | 1/1976 | Strickler et al. | 568/344 |
| 4,010,205 | 3/1977 | Becker et al. | 568/344 |
| 4,046,813 | 9/1977 | Brenner | 568/344 |
| 4,092,361 | 5/1978 | Costantini et al. | 568/344 |

FOREIGN PATENT DOCUMENTS

| 65707 | 12/1982 | European Pat. Off. | 568/343 |
| 2457157 | 7/1975 | Fed. Rep. of Germany | 568/344 |
| 643490 | 1/1979 | U.S.S.R. | 568/342 |

Primary Examiner—James H. Reamer
Attorney, Agent, or Firm—Oblon, Spivak, McClelland, Maier & Neustadt

[57] ABSTRACT

A process for preparing 3,5,5-trimethyl-4-hydroxy-2-cyclohexen-1-one, comprising:
  oxidizing beta-isophorone in the presence of hydrogen peroxide and a weak organic acid at a temperature in the range of 0°–100° C.

9 Claims, 1 Drawing Sheet

PROCESS FOR PREPARING 3,5,5,-TRIMETHYL-4-HYDROXY-2-CYCLOHEXEN-1-ONE

BACKGROUND OF THE INVENTION

1. Field of the Invention

The invention is directed to a process for the preparation of 4-hydroxyisophorone through the oxidation of beta-isophorone.

2. Discussion of the Background 3,5,5-Trimethyl-4-hydroxy-2-cyclohexen-1-one (4-hydroxyisophorone) is described in the literature as a fragrance for tobacco products (JP-OS 81 35 990; CH-PS 549 961; DE-OS 22 02 066), as a flavor and fragrance in foods (CH-PS 549 956; M. Ishihara et al., J. Org. Chem. 1986, 51, 491-5), and as a base material for the synthesis of various pharmaceuticals (N. S. Zarghami et al., Phytochemistry 1971, 10, 2755-61; J. N. Marx and F. Sondheimer, Tetrahedron, Suppl. No. 8, Pt 1, 1-7, 1966). It is generally synthesized by the oxidation of beta-isophorone (3,5,5-trimethyl-3-cyclohexen-1-one) by various methods.

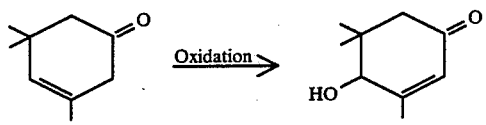

However, a severe limitation existed until recently because no practical procedure was known for preparing beta-isophorone and no further synthetic possibilities were studied. In accordance with DE-OS 37 35 211, however, beta-isophorone can now be prepared conveniently from alpha-isophorone (3,5,5-trimethyl-2-cyclohexen-1-one) by catalytic isomerization, so that at least this problem has been eliminated.

Oxidation in the para-position relative to the carbonyl group in these compounds produces a reactive substituent that permits further syntheses to obtain odorants and flavors identical to natural products, and to prepare Vitamin A derivatives. For this reason, the least expensive and chemically most economical method for carrying out this oxidation step was sought. It must be considered here that beta-isophorone rearranges (back-isomerizes) readily to alpha-isophorone, which does not undergo the desired reaction and is thus unavailable for producing 4-hydroxyisophorone. A need exists, therefore, for a method to keep back-isomerization within limits in addition to the other requirements mentioned.

It is well known that beta-isophorone can be oxidized by air using noble metal catalysts (FR-A 2 335 486). In addition to 4-ketoisophorone and alpha-isophorone, the desired 4-hydroxyisophorone is obtained in this reaction as a byproduct also. 4-Hydroxyisophorone can also be obtained directly from alpha-isophorone in small yields using a biochemical method with Aspergillus niger (JP-OS 81 35 990; Y. Mikami et al., Agric. Biol. Chem. 1981, 45, 791-3). A. Heymes and P. Teisseire obtained 4-hydroxyisophorone in 34% yield by oxidation with monoperphthalic acid (Recherches 1971, 18, 104-8), while N. S. Zarghami and D. E. Heinz (Phytochemistry 1971, 10, 2755-61) disclosed no yield information for the reaction with peracetic acid. J. N. Marx and F. Sondheimer report a yield of 87% from the treatment of beta-isophorone with m-chloroperbenzoic acid, but the recalculation of the results they reported shows only a yield of 56%, which is also in agreement with other information in the literature (Tetrahedron, Suppl. No. 8, Pt. 1, 1-7, 1966; see also O. Isler et al., Helv. Chim. Acta 39, 2041, 1956).

All of the methods published so far have serious deficiencies. On the one hand, the yields are poor, the chemicals used are costly, and it is difficult and expensive to isolate the end product; on the other hand, the processes have large amounts of waste. A technical process based on the available literature can thus be rather surely excluded.

SUMMARY OF THE INVENTION

Accordingly, one object of the present invention is to provide a process for the preparation of 4-hydroxyisophorone which may be carried out easily and uses inexpensive reagents.

This and other objects which will become apparent from the following specification have been achieved by the present process for producing 4-hydroxyisophorone in which beta-isophorone is oxidized in the presence of hydrogen peroxide and a weak organic acid at a temperature in the range from 0-100° C.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawing, wherein.

DETAILED DESCRIPTION OF THE PREFERRED EMBODIMENTS

Figure 1:
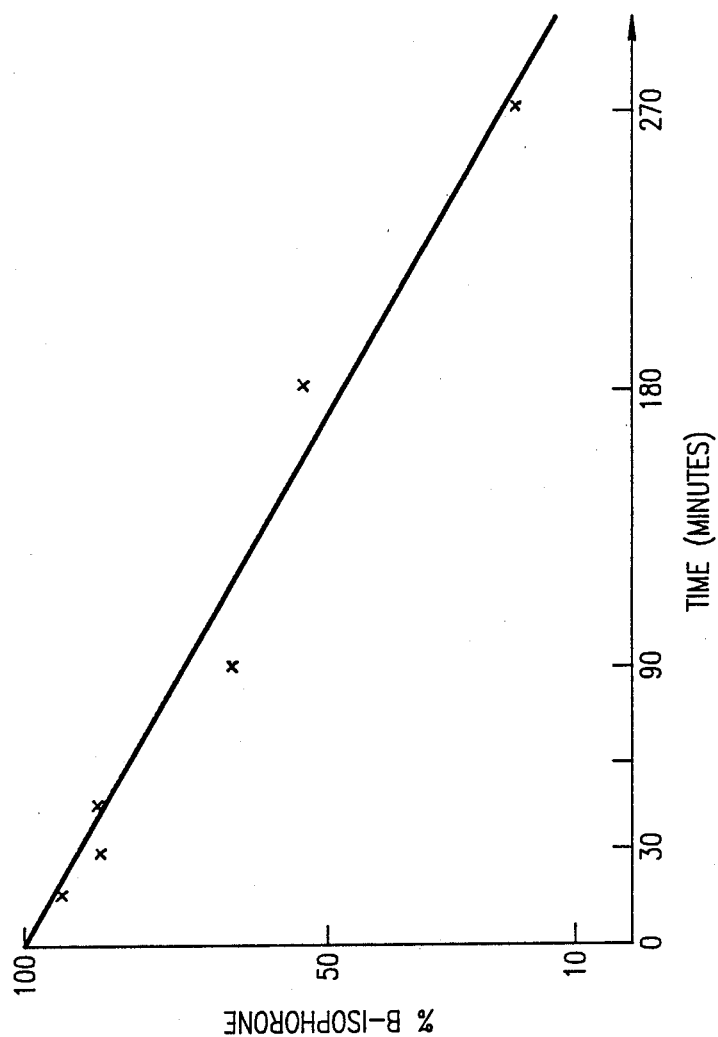
FIG. 1, illustrates the reformation of alpha-isophorone with time from an initial mixture of beta-isophorone and formic acid at room temperature.

It was found surprisingly that the oxidation of beta-isophorone to 4-hydroxyisophorone succeeds in the presence of hydrogen peroxide and even commercial hydrogen peroxide solution. The hydrogen peroxide concentration can be from about 25 to 45%, preferably about 30%.

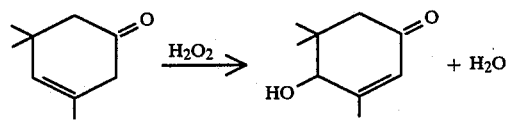

To prevent oxirane (epoxide) formation, which is known with this reaction, it is preferable to carry out the oxidation in acidic medium. An especially preferred acidic medium is prepared using a weak organic acid, for example formic acid. Other acids, especially inorganic acids, catalyze the back-isomerization of beta-isophorone to alpha-isophorone to a large extent. On the other hand, sufficient time remains for the oxidation of most of the beta-isophorone to 4-hydroxyisophorone when using the weaker formic acid. The diagram shown in FIG. 1 shows the time curve for the reformation of alpha-isophorone in an initial mixture of molar quantities of beta-isophorone and formic acid at room temperature.

Furthermore, weak organic acids, such as formic acid, have the advantage of better solubility for all of the reactants. Another benefit of the use of weak acids such as formic acid, is based on the fact that the excess hydrogen peroxide is positively destroyed, as shown in the equation below, in the subsequent processing and there is no risk of spontaneous peroxide decomposition.

$$H_2O_2 + HCOOH \rightarrow CO_2 + 2 H_2O$$

The reaction is controlled so that the conditions for reliable destruction of excess hydrogen peroxide are reached toward the end of the reaction. The reaction product can be separated after neutralization as an organic phase, and can be distilled.

The process of the present invention is relatively simple technically. Inexpensive commercial chemicals are used as reagents. For example, formic acid and 30% hydrogen peroxide solution are placed in a stirred apparatus in a molar ratio of from about 1:1 to about 5:1 in a temperature range between 0° C. and 100° C., and about 0.5 to 2.5 moles, preferably 1 mole of beta-isophorone is added slowly. The formic acid/hydrogen peroxide mixture may also be added to the beta-isophorone. Gentle cooling may be used to remove the heat of reaction, depending on the selected temperature conditions and batch size. After completing the reaction and allowing the reaction to stand, the batch, which has become homogeneous, is neutralized with a suitable base, such as for example an alkali or alkaline earth metal hydroxide, oxide, carbonate or bicarbonate. A preferred base is sodium bicarbonate. The upper phase that forms is separated, dried, and distilled under vacuum. After the separation of back-isomerized alpha-isophorone, 4-hydroxyisophorone is obtained as a distillate. The alpha-isophorone distilled off in the forerun can be recycled to the process after reisomerization according to DE-OS 37 35 211.

Other features of the invention will become apparent in the course of the following descriptions of the exemplary embodiments which are given for illustration of the invention and are not intended to be limiting thereof.

EXAMPLES

Example 1

120 g (2 moles) of 30% hydrogen peroxide solution is mixed with 48 g (1 mole) of formic acid, and 138 g (1 mole) of beta-isophorone is added over a period of ½ hour with stirring at 40° C. The reaction is allowed to continue at 40° C. (gentle external cooling and stirring), and after being allowed to stand for 12 hours, the mixture is heated for a short time (½ hour) at 80° C. The mixture is then neutralized with sodium bicarbonate, and the upper layer that forms is separated, dried with sodium sulfate, and distilled under vacuum.

The fractions obtained from the distillation are:

| | |
|---|---|
| Bp(4 mm Hg) = 68–92° C. | 44 g corresponding to 32% alpha-isophorone, and |
| Bp(0.2 mm Hg) = 124° C. | 72 g corresponding to 47% 4-hydroxyisophorone with $n_D^{20} = 1.5010$. |

Considering the conversion and the recovered alpha-isophorone, the yield is 69% of product.

EXAMPLES 2 AND 3

Examples 2 and 3 are carried out similarly to Example 1, but at a reaction temperature 60° C. (Example 2) or 80° C. (Example 3).

The amounts of product obtained are:
Example 2:
42 g corresponding to 31% alpha-isophorone, and
59 g corresponding to 39% 4-hydroxyisophorone.
The yield based on conversion is 66%.
Example 3:
46 g corresponding to 34% alpha-isophorone, and
63 g corresponding to 42% 4-hydroxyisophorone.
The yield based on conversion is 70%.

EXAMPLE 4

The procedure is similar to Example 1, but the amount of hydrogen peroxide solution used was increased to a molar ratio of hydrogen peroxide to beta-isophorone of 3:1. The amounts of product produced are then:
27 g corresponding to 20% alpha-isophorone, and
85 g corresponding to 56% 4-hydroxyisophorone.
The yield based on the conversion is calculated to be 82%.

Obviously, numerous modifications and variations of the present invention are possible in light of the above teachings. It is therefore to be understood that within the scope of the appended claims, the invention may be practiced otherwise than as specifically described herein.

What is new and desired to be secured by letters Patent of the United States.

1. A process for preparing 3,5,5-trimethyl-4-hydroxy-2-cyclohexen-1-one, comprising:
   oxidizing beta-isophorone in the presence of aqueous hydrogen peroxide and formic acid at a temperature in the range of 0°–100° C., wherein said hydrogen peroxide and said acid are present in a molar ratio of about 1:1 to about 5:1.

2. The process of claim 1, wherein said hydrogen peroxide solution contains about 25–45% hydrogen peroxide.

3. The process of claim 2, wherein said hydrogen peroxide solution contains about 30% hydrogen peroxide.

4. The process of claim 3, wherein said beta-isophorone is present in an amount from about 0.5–2.5 moles.

5. The process of claim 1, wherein said oxidizing step comprises mixing an aqueous solution containing about 30% hydrogen peroxide with said acid in a molar ratio of about 1:1 to about 5:1 and then contacting said mixture with about 0.5–2.5 moles of beta-isophorone.

6. The process of claim 5, wherein said mixture is contacted with about 1 mole of beta-isophorone.

7. The process of claim 1, further comprising neutralizing said oxidized beta-isophorone with a base.

8. The process of claim 7, wherein said base is selected from the group consisting of alkali and alkaline earth metal hydroxides, oxides, carbonates and bicarbonates.

9. The process of claim 8, wherein said base is sodium bicarbonate.

* * * * *